(12) United States Patent
Baloa Welzien et al.

(10) Patent No.: US 9,668,692 B2
(45) Date of Patent: Jun. 6, 2017

(54) APNEA AND HYPOPNEA DETECTION

(71) Applicant: Breathe Technologies, Inc., Irvine, CA (US)

(72) Inventors: Leonardo Alberto Baloa Welzien, Lake Forest, CA (US); Enrico Bambrilla, Irvine, CA (US); Samir S. Ahmad, San Diego, CA (US)

(73) Assignee: Breathe Technologies, Inc., Irvine, CA (US)

( * ) Notice: Subject to any disclaimer, the term of this patent is extended or adjusted under 35 U.S.C. 154(b) by 922 days.

(21) Appl. No.: 14/020,729

(22) Filed: Sep. 6, 2013

(65) Prior Publication Data

US 2015/0073291 A1 Mar. 12, 2015

(51) Int. Cl.
| | |
|---|---|
| *A61B 5/087* | (2006.01) |
| *A61M 16/06* | (2006.01) |
| *A61B 5/00* | (2006.01) |
| *A61M 16/00* | (2006.01) |

(52) U.S. Cl.
CPC .......... *A61B 5/4818* (2013.01); *A61B 5/4836* (2013.01); *A61M 16/0051* (2013.01); *A61M 16/0069* (2014.02); *A61B 5/087* (2013.01); *A61B 5/0871* (2013.01); *A61B 5/0878* (2013.01); *A61B 5/7282* (2013.01); *A61M 16/06* (2013.01); *A61M 2016/0027* (2013.01); *A61M 2205/3344* (2013.01); *A61M 2205/42* (2013.01); *A61M 2205/52* (2013.01)

(58) Field of Classification Search
CPC ... A61B 5/0871; A61B 5/0878; A61B 5/4818; A61B 5/4836; A61B 5/7282; A61B 5/08; A61B 5/087; A61B 5/0873; A61B 5/08091; A61M 16/0051; A61M 16/0069; A61M 16/06; A61M 2016/0027; A61M 2205/3344; A61M 2205/42; A61M 2205/52; A61M 2016/003; A61M 2016/0036

See application file for complete search history.

(56) References Cited

U.S. PATENT DOCUMENTS

| | | | |
|---|---|---|---|
| 5,335,654 | A | 8/1994 | Rapoport |
| 6,138,675 | A | 10/2000 | Berthon-Jones |
| 7,118,536 | B2 | 10/2006 | Haberland et al. |
| 7,168,429 | B2 | 1/2007 | Matthews et al. |
| 2005/0211249 | A1 | 9/2005 | Wagner et al. |
| 2012/0088992 | A1 | 4/2012 | Armistead |
| 2012/0179061 | A1 | 7/2012 | Ramanan et al. |

OTHER PUBLICATIONS

International Search Report and Written Opinion for PCT/US14/54142 (15 Pages). Issued Jan. 2, 2015.

*Primary Examiner* — Navin Natnithithadha
(74) *Attorney, Agent, or Firm* — Stetina Brunda Garred and Brucker; Mark B. Garred

(57) ABSTRACT

The identification of obstructed breathing, including an apnea condition and a hypopnea condition, is disclosed. A signal representative of a flow rate of therapeutic gas being delivered to the patient is received. A peak flow value and a minimum flow value over a predetermined time window encompassing a plurality of respiration cycles is derived. A polynomial difference equation from the peak flow values and the minimum flow values is generated, and a respiration index from a minimum of the polynomial difference equation is derived. The apnea and/or hypopnea condition is indicated based upon a comparison of the respiration index to a predefined obstruction threshold over a predefined obstruction time period.

24 Claims, 3 Drawing Sheets

APNEA AND HYPOPNEA DETECTION

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates generally to patient ventilation systems, and more particularly to methods and systems for apnea and hypopnea identification for continuous positive airway pressure (CPAP) therapy.

2. Related Art

The respiration system of the human body provides needed oxygen intake, oxygen/carbon dioxide exchange, and carbon dioxide expulsion functions, each of which involves the lungs. In this regard, the lungs function as a gas-exchanging organ in which inhaled oxygen is passed to the blood, and collected carbon dioxide is passed from the blood to the air. Additionally, the lungs function as a respiratory pump that transports oxygen-rich air into the lungs, and the carbon dioxide-rich air out of the lungs.

There has been an increasing trend in the number of individuals suffering from obstructive sleep apnea and hypopnea, which interrupts and/or reduces respiration during sleep. Apnea is understood to refer to a condition in which there is a complete obstruction of the airway that results in the cessation of airflow for ten seconds or more. These respiratory pauses may occur repetitively, and alleviated only when the patient jolted back to a partially awake state. A partial obstruction leads to hypopnea, which is understood to be a reduction of peak flow into or out of the lungs by 30% or more from the peak flow baseline during normal breathing for a duration of ten seconds or more. The obstruction typically occurs in the tongue, the soft palate, or the upper airway. Although some degree of apnea and/or hypopnea is considered normal, in more severe cases, daytime sleepiness, fatigue, and impaired alertness may result as a consequence of reduced blood oxygen saturation and constant interruptions to sleep cycles. Chronic sleep apnea/hypopnea can lead to more serious health concerns, including cardiac arrhythmias, hypertension, and congestive heart failures with high mortality rates. Numerous cognitive functions are adversely affected as well.

Conventional treatments for sleep apnea may involve the prescription of one or more of a weight loss regimen (as apnea and hypopnea is closely correlated to obesity), medication, oral appliances, continuous positive airway pressure (CPAP) therapy, and less commonly, surgery. Generally, CPAP involves the application of positive pressure to open the patient's airway to prevent its collapse, as would otherwise occur during apnea. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway. However, supplying positive pressure flow into the patient during the expiratory phase generates resistance to the patient's breathing efforts, causing discomfort. Furthermore, toward the end of the patient's expiratory phase, flow and pressure in the airway is naturally minimal, such that positive pressure can cause additional discomfort. Notwithstanding the clinician's best efforts to prescribe a CPAP treatment flow rate that minimizes such extraneous pressure augmentation while ensuring the proper splinting of the airway during inspiration, the patient is still subject to higher pressures than needed throughout the breathing cycle. Accordingly, improvements that vary the delivered pressure according to breathing cycles or to patient efforts have also been developed.

The detection of abnormal breathing can be achieved with a variety of techniques. One involves measuring inspiration and expiration pressure over time, with running averages being compared to instantaneous measurements to determine whether any one cycle is outside a predetermined threshold. Information from multiple sensors, including nasal pressure, pulse oximetry, and plethysmograph sensors, is necessary to make accurate assessments. Instead of pressure measurements, systems such as those disclosed in U.S. Pat. No. 6,138,675 to Berthon-Jones are known to use flow measurements, though variances from a measured average over a time window are still relied upon to detect apnea.

Conventional CPAP devices that are intended for daily home use do not utilize an extensive number of sensors for cost reasons, and accordingly control is often based upon a single flow signal derived from pressure measurements or an estimated flow signal derived from a mathematical model corresponding to the operational parameters of the ventilation source, i.e., the blower motor. Accordingly, there is a need in the art for detecting apnea and hypopnea conditions with the single flow sensor measurement.

BRIEF SUMMARY

The present disclosure contemplates the determination of an apnea condition or a hypopnea condition for patients using a continuous positive airway pressure (CPAP) device. This determination may be based upon a mathematical model from flow information captured over a time window that is compared to various established criteria. One embodiment is directed to a method that includes a step of receiving from a signal representative of a flow rate of therapeutic gas being delivered to the patient for a predetermined time window over a plurality of respiration cycles. The method may also include deriving a peak flow value of each of the respiration cycles within the predetermined time window. There may also be a companion step of deriving a minimum flow value of each of the respiration cycles within the predetermined time window. The method may include generating a polynomial difference function from the peak flow values of a plurality of the respiration cycles in the predetermined window and the minimum flow values of a plurality of the respiration cycles in the predetermined window. Then, the method may include deriving a respiration index from a minimum of the polynomial difference function. There may further be a step of indicating the at least one of the apnea condition and the hypopnea condition based upon a comparison of the respiration index to a predefined obstruction threshold over a predefined obstruction time period.

Another embodiment of the present disclosure is similarly directed to a method for identifying obstructed breathing by a patient undergoing continuous positive airway pressure therapy. Accordingly, there may be a corresponding step of receiving signal representative of a flow rate of therapeutic gas being delivered to the patient for a predetermined time window over a plurality of respiration cycles. There is also a step of deriving a peak flow value of each of the respiration cycles within the predetermined time window. Thereafter, the method may include deriving a minimum flow value of each respiration cycle within the predetermined time window. The method may include a step of generating a polynomial difference function from the peak flow values of a plurality of the respiration cycles in the predetermined window and the minimum flow values of a plurality of the respiration cycles in the predetermined window. There may be a step of deriving an apnea index from a minimum of the polynomial difference function. If the apnea index is less than a predefined apnea threshold over a predefined time period, the method may proceed to a step of indicating an apnea condition. Moreover, if the apnea index is greater than the predefined apnea threshold over the predefined time period, the method may include a step of deriving a hypopnea index corresponding to a fraction of the minimum of the polynomial difference function. In turn, if the hypopnea index is greater than a predefined hypopnea threshold after an elapse of a hypopnea time threshold, the method may include a step of indicating a hypopnea condition.

Certain other embodiments of the present disclosure contemplate respective computer-readable program storage media that each tangibly embodies one or more programs of instructions executable by a data processing device to perform the foregoing methods. The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of the presently preferred embodiment of apnea and hypopnea detection, and is not intended to represent the only form in which the presented embodiments may be developed or utilized. It is further understood that the use of relational terms such as first and second and the like are used solely to distinguish one from another entity without necessarily requiring or implying any actual such relationship or order between such entities.

Figure 1:
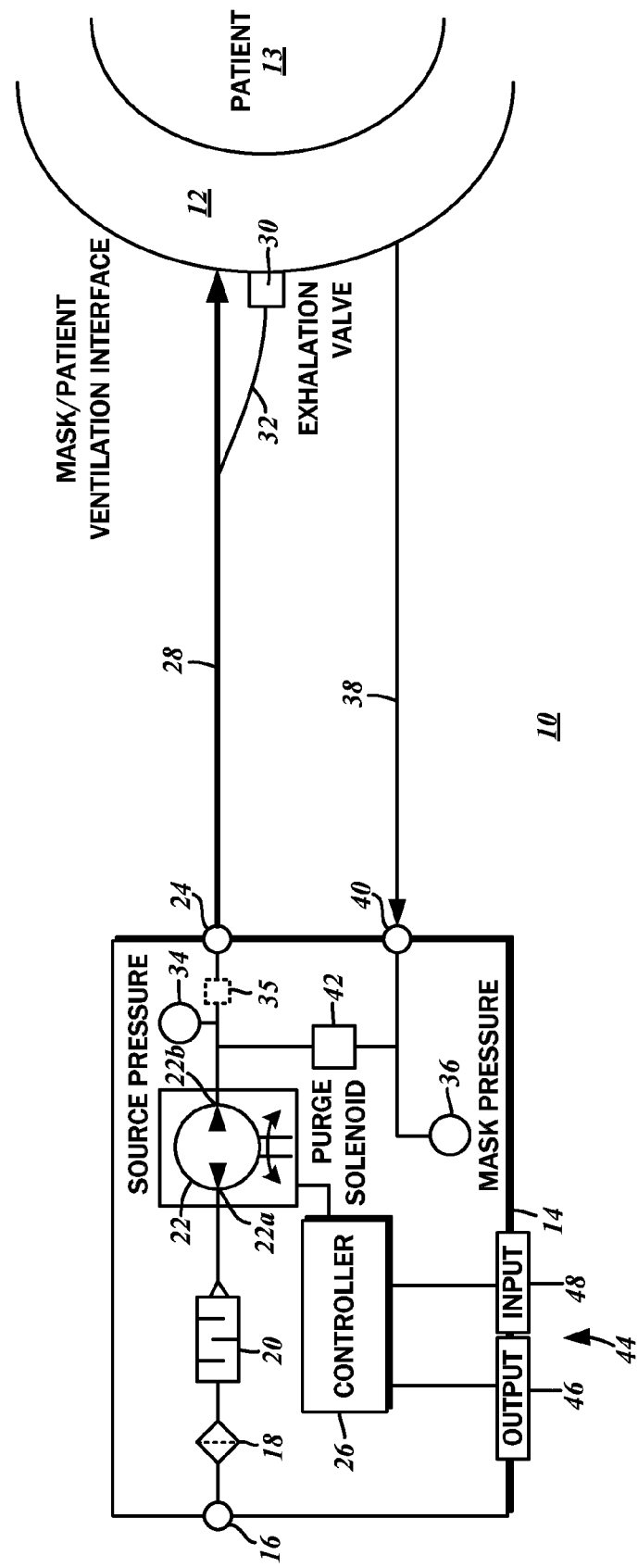
FIG. 1 is a block diagram showing the components of a ventilator apparatus in accordance with various embodiments of the present disclosure including a ventilation unit, a patient ventilation interface, gas passage conduits, and oxygen sources.

The block diagram of FIG. 1 illustrates an exemplary respiratory assistance device 10 in which various embodiments of the present disclosure may be implemented. There is a mask or patient ventilation interface 12, and a ventilation unit 14. The patient ventilation interface 12 is understood to be an apparatus such as a full-face mask or a nasal pillows mask that can be placed in direct gas flow communication with the upper respiratory tract, i.e., the nasal cavity and/or the oral cavity, of a patient 13. It will be appreciated that other apparatuses that so interface the respiratory tract of the patient 13 to the ventilation unit 14 may be substituted without departing from the scope of the present disclosure.

The ventilation unit 14 generates a flow of breathing gas that is delivered to the patient via the patient ventilation interface 12. The breathing gas may be ambient air a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a ventilation source 22, which may be a centrifugal fan, blower, or any other suitable device that generates gas flow and pressure suitable for CPAP treatment in accordance with the present disclosure. The ventilation source 22 has an inlet port 22a coupled to the sound suppressor 20, and an outlet port 22b that is in gas flow communication with an outlet port 24 of the ventilation unit 14. The ventilation source 22 is driven electrically and its actuation is governed by a controller 26, which implements the various functionalities described in further detail below.

The flow of breathing gas that is output from the ventilation source 22 is passed through the outlet port 24 to a gas conduit 28 that is in coupled to the aforementioned patient ventilation interface 12. The gas conduit 28 is understood to be a plastic tube having a predetermined inner diameter such as 22 mm or smaller, though any other conduit of suitable material and construction may be utilized. The patient ventilation interface 12 in accordance with various embodiments of the present disclosure also includes a piloted exhalation valve 30 that is selectively actuated depending on the pressure differential between the patient ventilation interface 12 and the ventilation unit 14. The exhalation valve 30 is connected to a pilot line 32 that branches from the gas conduit 28. A pressure difference is generated between the patient ventilation interface and the exhalation valve, such that it is closed during inspiration and opened during expiration. It will be appreciated that the specifics of the patient ventilation interface 12, including the piloted exhalation valve 30 thereof, are presented by way of example only and not of limitation. Any other suitable patient ventilation interface 12, including those that may be utilized in conjunction with different variations of the ventilation unit 14, may be substituted without departing from the scope of the present disclosure.

In one embodiment of the presently contemplated ventilation system 10, there are dual pressure sensors, including a source pressure sensor 34 and a patient interface pressure sensor 36. The source pressure sensor 34 is disposed within the ventilation unit 14, and monitors the pressure at the ventilation source output port 22b. The patient interface pressure sensor 36 is also physically disposed within the ventilation unit 14, but is in direct gas flow communication with the patient ventilation interface 12 over a pressure sensing line 38 that is connected to a sensor inlet port 40 of the ventilation unit 14. When the ventilation unit 14 is operating, gas pressure within the pressure sensing line 38 as well as the gas conduit 28 may be connected to deliver a purge flow to clear the pressure sensing line 38. This can be done through a purge solenoid 42 connected to both. The purge can be continuous or intermittent according to the patient's breathing phase or pressure difference between the valve pressure and the patient interface pressure. Optionally, either in addition to the dual pressure sensors 34, 36, or as a replacement for the source pressure sensor 34, a flow sensor 35 may be in pneumatic communication with the output 22b of the ventilation source 22 and the gas conduit 28 to measure airflow through the same.

The present disclosure contemplates the detection of an apnea or hypopnea condition of the patient 13, who is undergoing CPAP treatment. As indicated above, earlier techniques utilized actual flow data, but an improved, alternative modality that employs a mathematical model from the captured flow data is envisioned. With reference to the flowchart of FIG. 2, the method commences with a step 300 of receiving a signal representative of a flow rate of therapeutic gas being delivered to the patient 13. Again, this signal may be produced by the aforementioned flow sensor 35. In the alternative, this signal may be an approximation based upon a function dependent on another measured variable such as pressure readings from the pressure sensors 34, 36, the speed of the ventilation source 22, temperature readings from a thermistor, and so forth. However it may be generated, so long as the patient 13 is undergoing CPAP therapy, the signal representative of the flow rate may be continually received. In the subsequent, additional steps toward determining respiratory obstruction, it is understood that only a subset of all of the received flow rate signals need be utilized. In particular, there may be a moving window of a predetermined duration that encompasses at least one patient respiration cycle, i.e., a complete inspiration and expiration.

Figure 3:
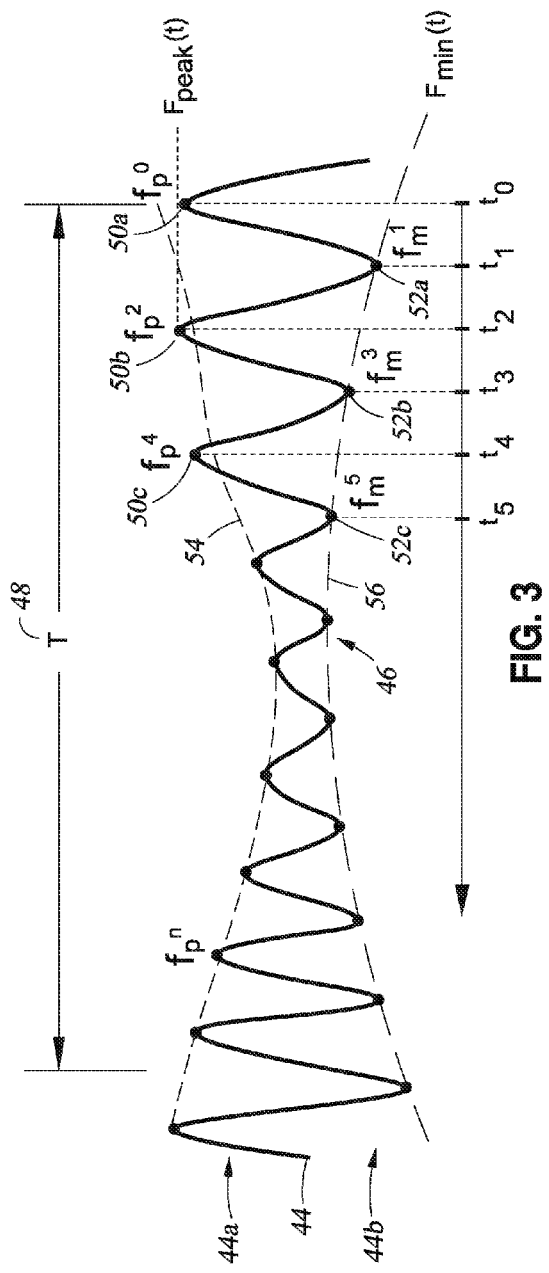
FIG. 3 is a flow rate graph of several respiratory cycles over a time window, including several cycles that are obstructed.

With reference to the graph of FIG. 3, an exemplary flow rate plot 44 shows multiple respiratory cycles characterized by a positive flow rate 44a during inspiration, and a negative flow rate 44b during expiration. It will be appreciated that the flow rate plot 44 is an example only, and different patients 13 may exhibit different respiration patterns. The flow rate plot 44 also indicates a region of reduced airflow 46 in both inspiration and expiration, which corresponds to a hypopnea condition. Quantified, hypopnea airflow is understood to be approximately 30% of the peak airflow. When airflow completely stops, that is, the flow measurements are approximately zero, there is understood to be an apnea condition. It is understood that an apnea or hypopnea is indicated when this condition persists for ten seconds or more. As mentioned earlier, flow data inside a moving window is utilized in determining obstructed respiration, and this moving window is defined as a time period T 48.

Figure 2:
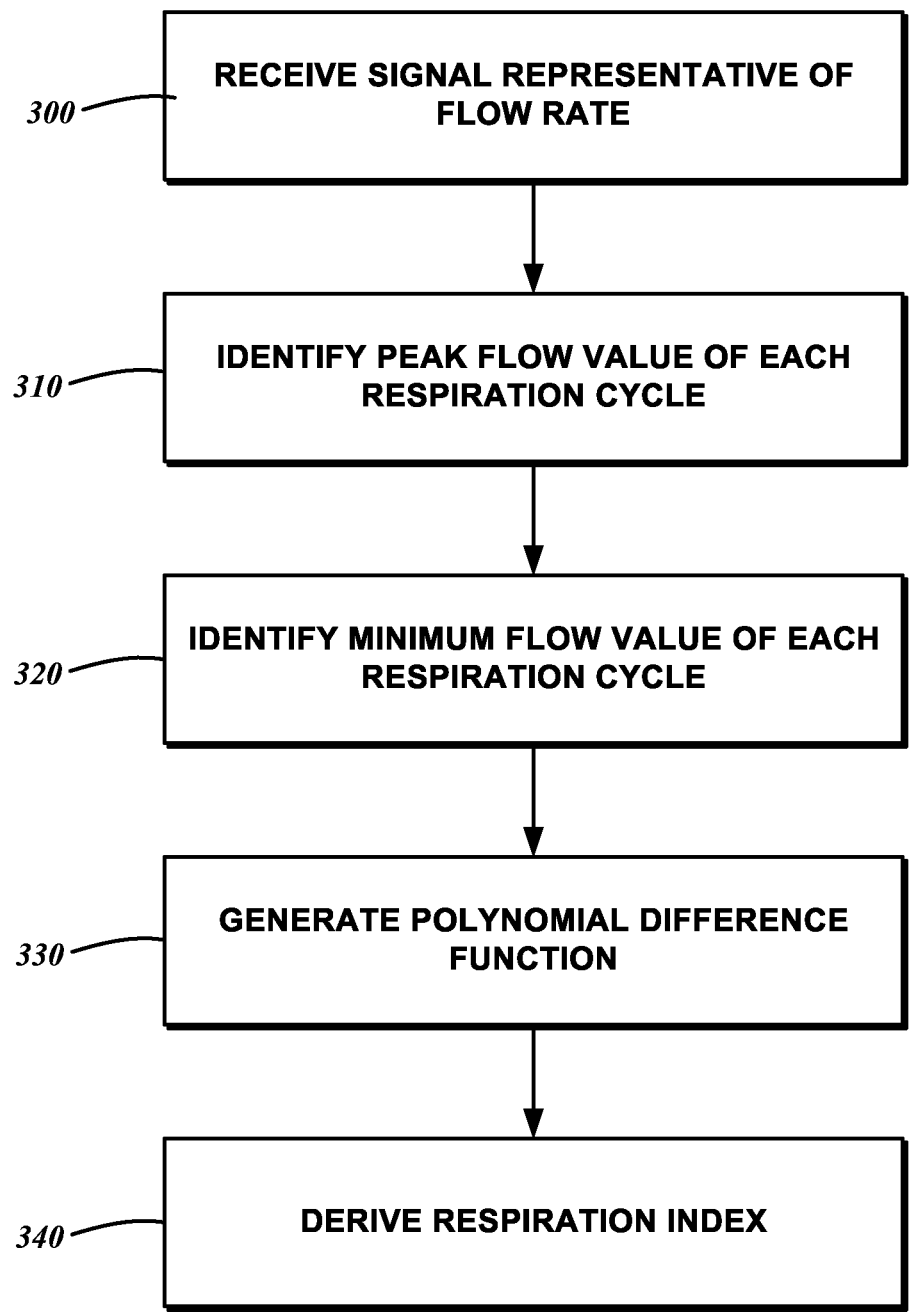
FIG. 2 is a flowchart illustrating one embodiment of a method for identifying obstructed breathing by a patient.

Referring back to the flowchart of FIG. 2, the method continues with a step 310 of deriving a peak flow value of each respiration cycle, as well as a companion step 320 of deriving a minimum flow value of each respiration cycle. As utilized herein, the deriving is understood to encompass any operation which results in the respective peak or minimum flow values being identified and stored for subsequent use in other steps. It is not intended to be limited to generating derivatives, or any particular mathematical operation. With reference again to the graph of FIG. 3, the peak flow values include a first peak 50a at a time $t_0$, a second peak 50b at a time $t_2$, a third peak 50c at a time $t_4$, and so forth. Similarly, the minimum flow values include a first minimum 52a occurring at time $t_1$, a second minimum 52b occurring at time $t_3$, and a third minimum 52c occurring at a time $t_5$, and so forth. Any suitable method for locating minimum and maximum values in a periodic signal may be utilized, such as identifying transitions between negative and positive derivatives of the raw flow signal.

Following the identification of the peak flow values and minimum flow values, the method continues with a step 330 of generating a polynomial difference function therefrom. In further detail, there may be a preliminary step of generating a peak flow polynomial function from the peak flow values 50 of each respiration cycle in the time window T 48, visualized as a peak polynomial function plot 54. Likewise, there may be another preliminary step of generating a minimum flow polynomial function from the minimum flow values 52 of each respiration cycle in the same time window T 48. The minimum polynomial function is shown as a plot 56. The number of values to use for generating the respective polynomial functions can be varied.

Figure 4:
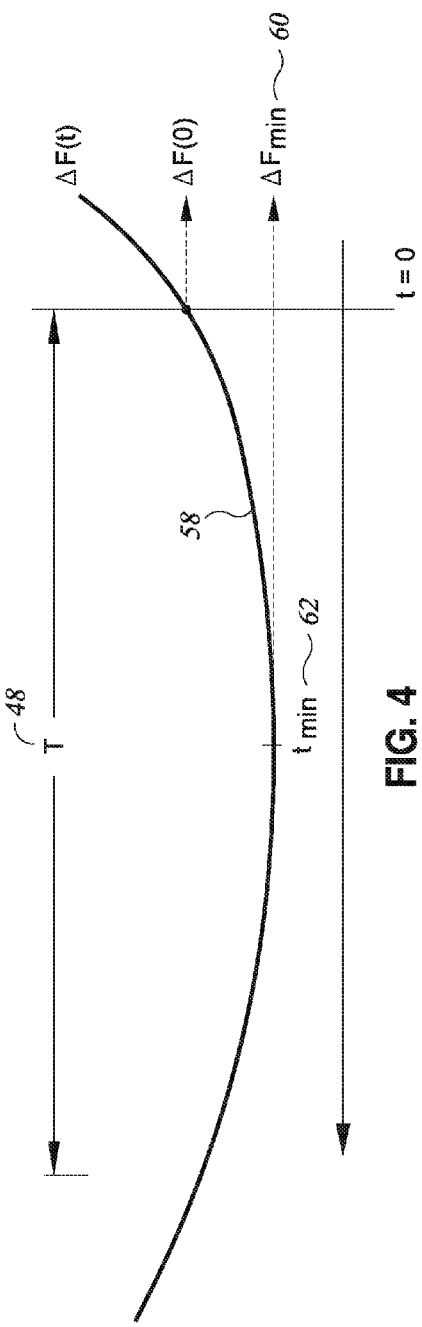
FIG. 4 is a graph showing a polynomial difference function of peak and minimum flow values over the same time window shown in the graph of FIG. 3.

In accordance with various embodiments of the present disclosure, a least square estimation may be used to derive a second order polynomial. As indicated above, the flow values may be recorded together with the corresponding time. For example, the peak flow values may be provided as an ordered list of two variables: $\{(t_0, f_p^{\,0}), (t_2, f_p^{\,2}), \ldots (t_n, f_p^{\,n})\}$ and so on. The minimum flow values may also be provided as an ordered list of two variables: $\{(t_1, f_m^{\,1}), (t_3, f_m^{\,-3}) \ldots (t_n, f_m^{\,n})\}$, and so on. Given this data, the values of the parameters of the second order polynomials that represent best fits can be identified. In particular, the peak flow polynomial function, $F_p(t)$, is defined by $p_0 + p_1 t + p_2 t^2$, while the minimum flow polynomial function, $F_m(t)$, is defined by $m_0 + m_1 t + m_2 t^2$. The polynomial difference function, $\Delta F(t)$ is obtained by subtracting the minimum flow polynomial function, $F_m(t)$, from the peak flow polynomial function $F_p(t)$. The graph of FIG. 4 shows a plot 58 of the polynomial difference function.

Once the polynomial difference function is generated, the method continues with a step 340 of deriving a respiration index from a minimum 60 of the polynomial difference function over the time window T 48. Thus, this minimum ($\Delta F_{min}$) may be defined as $\min_T \Delta F(t)$ or $\Delta F(t_{min})$. Following the determination of the respiration index, step 350 of the method contemplates indicating at least one of an apnea condition and a hypopnea condition based upon such a comparison of the respiration index to various thresholds.

In order to detect the apnea condition, an apnea index, that is, the respiration index that corresponds to the minimum of the polynomial difference function ($\Delta F_{min}$) is compared against an apnea threshold ($\Delta F_{threshold}$). If the apnea index is less than the apnea threshold, then one of the conditions for indicating an apnea condition is satisfied. The other condition is if the apnea state lasts for longer than a predetermined duration. Specifically, the assessment made is whether the apnea index at a subsequent time corresponding to an apnea time threshold after the initial time corresponding to the minimum, is less than the same apnea threshold. Where $t_{min}$ 62 is the time at which the polynomial difference function is at a minimum ($\Delta F_{min}$), and $t_{apnea}$ is the apnea time threshold, then the polynomial difference function at the subsequent time is given by $\Delta F(t_{min} + t_{apnea})$. If that value is also less than the apnea threshold, it is understood that the apnea condition has continued at least the threshold duration. In accordance with various embodiments of the present disclosure, the threshold duration is ten seconds, though alternative durations may be substituted without departing from the scope of the present disclosure. With both the magnitude and the duration of the obstructed breathing corresponding to apnea, the apnea condition is indicated. Various references to inequality terms herein such as less than, less than or equal to, greater than, or greater than or equal to are intended to be interchangeable, and the threshold values for such operands may be adjusted to accommodate the same.

The indicating of the hypopnea condition occurs once it has been determined that an apnea condition does not exist. The determination of whether or not the hypopnea condition exists is also based upon a comparison of a different respiration index, which is separately referred to as a hypopnea index, against another predefined obstruction threshold over a predefined obstruction period. Although this different respiration index, i.e., the hypopnea index, is also derived from a minimum of the polynomial difference function, there are other components involved. More particularly, the hypopnea index is a ratio between the change in the polynomial difference function from the minimum ($\Delta F_{min}$) to the most recent breathing cycle $\Delta F(t_0)$, and the minimum ($\Delta F_{min}$). This ratio may be expressed as follows: $[\Delta F(t_0)-(\Delta F_{min})/(\Delta F_{min})]$. If the hypopnea index is greater than that a predefined hypopnea threshold, one of the conditions for indicating hypopnea is satisfied. Generally, this condition is intended to identify a significant drop in flow rates that indicates hypopnea. According to another embodiment of the present disclosure, this condition may also be defined as the minimum of the polynomial difference function ($\Delta F_{min}$) being less than or equal to a certain percentage of the polynomial difference function when initially measured ($\Delta F(t_0)$) or when it reaches the threshold (($\Delta F(t_{threshold})$) The other condition is where the hypopnea condition continues for a longer time period than a predetermined threshold, i.e., $t_h$ is greater than or equal to a $T_{threshold}$. If any one of the foregoing conditions are not satisfied, normal breathing is indicated.

The particulars shown herein are by way of example and for purposes of illustrative discussion of the embodiments of the disclosure only and are presented in the cause of providing what is believed to be the most useful and readily understood description of the principles and conceptual aspects of flow limitation detection. In this regard, no attempt is made to show details with more particularity than is necessary for the fundamental understanding of the present disclosure, the description taken with the drawings making apparent to those skilled in the art how the several forms of the present disclosure may be embodied in practice.

What is claimed is:

1. A method for identifying obstructed breathing by a patient undergoing continuous positive airway pressure therapy, including at least one of an apnea condition and a hypopnea condition, the method comprising:
   receiving a signal representative of a flow rate of therapeutic gas being delivered to the patient for a predetermined time window over a plurality of respiration cycles;
   deriving a peak flow value of each of the respiration cycles within the predetermined time window;
   deriving a minimum flow value of each of the respiration cycles within the predetermined time window;
   generating a polynomial difference function from the peak flow values of a plurality of the respiration cycles in the predetermined window and the minimum flow values of a plurality of the respiration cycles in the predetermined window;
   deriving a respiration index from a minimum of the polynomial difference function;
   indicating the at least one of the apnea condition and the hypopnea condition based upon a comparison of the respiration index to a predefined obstruction threshold over a predefined obstruction time period; and
   actuating a ventilation source of the therapeutic gas in accordance with the indicated at least one of the apnea condition and the hypopnea condition.

2. The method of claim 1, wherein the signal representative of the flow rate is an actual measured flow rate from a flow sensor.

3. The method of claim 1, wherein the signal representative of the flow rate is a derived flow rate from a sensor measuring a respiration condition of the patient.

4. The method of claim 3, wherein the respiration condition is pressure, and the sensor is a pressure sensor.

5. The method of claim 3, wherein the respiration condition is temperature, and the sensor is a thermistor.

6. The method of claim 1, further comprising:
   generating a peak flow polynomial function from the peak flow values of each respiration cycle in the predetermined time window; and
   generating a minimum flow polynomial function from the minimum flow values of each respiration cycle in the predetermined time window;
   wherein the polynomial difference function is generated from the peak flow polynomial function and the minimum flow polynomial function.

7. The method of claim 1, wherein:
   the respiration index is an apnea index equal to the minimum of the polynomial difference function; and
   the predefined obstruction threshold is an apnea threshold.

8. The method of claim 7, wherein the apnea condition is indicated when the apnea index is less than the apnea threshold.

9. The method of claim 1, wherein:
   the respiration index is a hypopnea index that is a fraction of the minimum of the polynomial difference function; and
   the predetermined obstruction threshold is a hypopnea threshold.

10. The method of claim 9, wherein the hypopnea condition is indicated when the hypopnea index is less than the apnea threshold.

11. The method of claim 1, wherein the polynomial difference function is a second order polynomial difference function.

12. A method for identifying obstructed breathing by a patient undergoing continuous positive airway pressure therapy, the method comprising:
   receiving a signal representative of a flow rate of therapeutic gas being delivered to the patient for a predetermined time window over a plurality of respiration cycles;
   deriving a peak flow value of each respiration cycle within the predetermined time window;
   deriving a minimum flow value of each respiration cycle within the predetermined time window;
   generating a polynomial difference function from the peak flow values of a plurality of the respiration cycles in the predetermined window and the minimum flow values of a plurality of the respiration cycles in the predetermined window;
   deriving an apnea index from a minimum of the polynomial difference function;

if the apnea index is less than a predefined apnea threshold over a predefined time period, indicating an apnea condition; and actuating a ventilation source of the therapeutic gas in accordance with the indicated apnea condition.

13. The method of claim 12, further comprising:

if the apnea index is greater than the predefined apnea threshold over the predefined time period, deriving a hypopnea index corresponding to a fraction of the minimum of the polynomial difference function; and if the hypopnea index is greater than a predefined hypopnea threshold after an elapse of a hypopnea time threshold, indicating a hypopnea condition.

14. The method of claim 13, further comprising:

if the apnea index is less than the predefined apnea threshold over the predefined time period and if the hypopnea index is less than the predefined hypopnea threshold after an elapse of hypopnea time threshold, indicating a normal respiration condition.

15. The method of claim 12, further comprising:

generating a peak flow polynomial function from the peak flow values of each respiration cycle in the predetermined time window; and generating a minimum flow polynomial function from the minimum flow values of each respiration cycle in the predetermined time window;

wherein the polynomial difference function is generated from the peak flow polynomial function and the minimum flow polynomial function.

16. The method of claim 12, wherein the signal representative of the flow rate is an actual measured flow rate from a flow sensor.

17. The method of claim 12, wherein the polynomial difference function is a second order polynomial difference function.

18. The method of claim 12, wherein the signal representative of the flow rate is a derived flow rate from a sensor measuring a respiration condition of the patient.

19. An article of manufacture comprising a program storage medium readable by a data processing apparatus, the medium tangibly embodying one or more programs of instructions executable by the data processing apparatus to perform a method for identifying obstructed breathing by a patient undergoing continuous positive airway pressure therapy, including at least one of an apnea condition and a hypopnea condition, the method comprising:

receiving from a signal representative of a flow rate of therapeutic gas being delivered to the patient for a predetermined time window over a plurality of respiration cycles;

deriving a peak flow value of each respiration cycle within the predetermined time window;

deriving a minimum flow value of each respiration cycle within the predetermined time window;

generating a polynomial difference function from the peak flow values of a plurality of the respiration cycles in the predetermined window and the minimum flow values of a plurality of the respiration cycles in the predetermined window;

deriving a respiration index from a minimum of the polynomial difference function;

indicating the at least one of the apnea condition and the hypopnea condition based upon a comparison of the respiration index to a predefined obstruction threshold over a predefined obstruction time period; and actuating a ventilation source of the therapeutic gas in accordance with the indicated at least one of the apnea condition and the hypopnea condition.

20. The article of manufacture of claim 19 wherein:

the respiration index is an apnea index equal to the minimum of the polynomial difference function;

the predefined obstruction threshold is an apnea threshold; and the apnea condition is indicated when the apnea index is less than the apnea threshold.

21. The article of manufacture of claim 19, wherein:

the respiration index is a hypopnea index that is a fraction of the minimum of the polynomial difference function;

the predetermined obstruction threshold is a hypopnea threshold; and the hypopnea condition is indicated when the hypopnea index is less than the apnea threshold.

22. The article of manufacture of claim 19, wherein the signal representative of the flow rate is an actual measured flow rate from a flow sensor.

23. The article of manufacture of claim 19, wherein the signal representative of the flow rate is a derived flow rate from a sensor measuring a respiration condition of the patient.

24. The article of manufacture of claim 19, wherein the polynomial difference function is a second order polynomial difference function.

* * * * *